(12) United States Patent
Gliner et al.

(10) Patent No.: US 9,168,004 B2
(45) Date of Patent: Oct. 27, 2015

(54) MACHINE LEARNING IN DETERMINING CATHETER ELECTRODE CONTACT

(75) Inventors: Vadim Gliner, Haifa (IL); Assaf Govari, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 347 days.

(21) Appl. No.: 13/589,347

(22) Filed: Aug. 20, 2012

(65) Prior Publication Data

US 2014/0051959 A1    Feb. 20, 2014

(51) Int. Cl.
| | |
|---|---|
| *A61B 5/00* | (2006.01) |
| *A61B 5/053* | (2006.01) |
| *A61B 18/14* | (2006.01) |
| *A61B 5/042* | (2006.01) |
| *A61B 17/00* | (2006.01) |
| *A61B 18/00* | (2006.01) |
| *A61B 19/00* | (2006.01) |

(52) U.S. Cl.
CPC ............. *A61B 5/6869* (2013.01); *A61B 5/0538* (2013.01); *A61B 5/6885* (2013.01); *A61B 5/7267* (2013.01); *A61B 18/1492* (2013.01); *A61B 5/0422* (2013.01); *A61B 5/6852* (2013.01); *A61B 2017/00026* (2013.01); *A61B 2017/00044* (2013.01); *A61B 2017/00243* (2013.01); *A61B 2018/00357* (2013.01); *A61B 2018/00577* (2013.01); *A61B 2018/00666* (2013.01); *A61B 2018/00869* (2013.01); *A61B 2018/00875* (2013.01); *A61B 2018/00904* (2013.01); *A61B 2019/465* (2013.01); *A61B 2019/5251* (2013.01)

(58) Field of Classification Search
USPC ............................................ 600/374; 606/41
See application file for complete search history.

(56) References Cited

U.S. PATENT DOCUMENTS

| | | |
|---|---|---|
| 6,226,542 B1 | 5/2001 | Reisfeld |
| 6,241,724 B1 | 6/2001 | Fleischman et al. |
| 6,301,496 B1 | 10/2001 | Reisfeld |
| 6,391,024 B1 | 5/2002 | Sun et al. |
| 6,695,808 B2 | 2/2004 | Tom |
| 6,814,733 B2 | 11/2004 | Schwartz et al. |
| 6,892,091 B1 | 5/2005 | Ben-Haim et al. |
| 6,915,149 B2 | 7/2005 | Ben-Haim |
| 6,997,924 B2 | 2/2006 | Schwartz et al. |
| 7,156,816 B2 | 1/2007 | Schwartz et al. |
| 7,306,593 B2 | 12/2007 | Keidar et al. |
| 7,536,218 B2 | 5/2009 | Govari et al. |
| 7,756,576 B2 | 7/2010 | Levin |
| 2007/0100332 A1 | 5/2007 | Paul et al. |

(Continued)

OTHER PUBLICATIONS

U.S. Appl. No. 13/343,024, filed Jan. 4, 2012, inventors: Assaf Govari et al.

(Continued)

*Primary Examiner* — Carl H Layno
*Assistant Examiner* — Jennifer Ghand

(57) ABSTRACT

Cardiac catheterization is carried out by memorizing a designation of a contact state between an electrode of the probe and the heart wall as one of an in-contact state and an out-of-contact state, and making a series of determinations of an impedance phase angle of an electrical current passing through the electrode and another electrode, identifying maximum and minimum phase angles in the series, and defining a binary classifier adaptively as midway between the extremes. A test value is compared to the classifier as adjusted by a hysteresis factor, and a change in the contact state is reported when the test value exceeds or falls below the adjusted classifier.

9 Claims, 5 Drawing Sheets

(56) References Cited

U.S. PATENT DOCUMENTS

| | | |
|---|---|---|
| 2008/0275465 A1 | 11/2008 | Paul et al. |
| 2008/0288038 A1 | 11/2008 | Paul et al. |
| 2008/0312521 A1 | 12/2008 | Solomon |
| 2008/0312713 A1* | 12/2008 | Wilfley et al. ................. 607/41 |
| 2013/0172875 A1 | 7/2013 | Govari et al. |

OTHER PUBLICATIONS

European Search Report mailed on Nov. 11, 2013 from corresponding European Patent Application No. 13180877.6.

* cited by examiner

MACHINE LEARNING IN DETERMINING CATHETER ELECTRODE CONTACT

FIELD OF THE INVENTION

This invention relates to tissue ablation systems. More particularly, this invention relates to monitoring of contact between an invasive probe and tissue within the body.

DESCRIPTION OF THE RELATED ART

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

U.S. Pat. No. 7,306,593, issued to Keidar et al., which is herein incorporated by reference, describes a method for ablating tissue in an organ by contacting a probe inside the body with the tissue to be ablated, and measuring one or more local parameters at the position using the probe prior to ablating the tissue. A map of the organ is displayed, showing, based on the one or more local parameters, a predicted extent of ablation of the tissue to be achieved for a given dosage of energy applied at the position using the probe. The given dosage of energy is applied to ablate the tissue using the probe, and an actual extent of the ablation at the position is measured using the probe subsequent to ablating the tissue. The measured actual extent of the ablation is displayed on the map for comparison with the predicted extent.

Impedance-based methods for assessing catheter-tissue contact that are known in the art typically rely on measurement of the magnitude of the impedance between an electrode on the catheter and a body-surface electrode. When the magnitude is below some threshold, the electrode is considered to be in contact with the tissue. This sort of binary contact indication may be unreliable, however, and is sensitive to changes in the impedance between the body-surface electrode and the skin.

U.S. Patent Application Publication Nos. 2008/0288038 and 2008/0275465, both by Sauarav et al., which are herein incorporated by reference, describe an electrode catheter system, which may comprise an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

SUMMARY OF THE INVENTION

There is provided according to embodiments of the invention a method of cardiac catheterization, which is carried out by inserting a probe into a heart of a living subject, and memorizing a designation of a contact state between an electrode of the probe and the heart wall as one of an in-contact state and an out-of-contact state. The method is further carried out by while the electrode is at the wall by passing an electrical current between the electrode and another electrode, making at least three determinations of an impedance phase angle of the electrical current, identifying a maximum phase angle and a minimum phase angle among the determinations, and defining a binary classifier as a value that is intermediate the minimum phase angle and the maximum phase angle. The method is further carried out, when the designation of the contact state is the in-contact state, by changing the designation to the out-of-contact state when another of the determinations is less than the binary classifier by at least a first hysteresis factor. The method is further carried out, when the designation of the contact state is the out-of-contact state, by changing the designation to the in-contact state when the other of the determinations is greater than the binary classifier by at least a second hysteresis factor, and reporting the changed designation.

According to an aspect of the method, the other of the determinations is the most recent determination.

Still another aspect of the method includes determining that a difference between the minimum phase angle and the maximum phase angle exceeds a predefined noise threshold.

According to an additional aspect of the method, the value of the binary classifier is midway between the minimum phase angle and the maximum phase angle.

According to one aspect of the method, the first hysteresis factor is equal to the second hysteresis factor.

Yet another aspect of the method includes reporting an unchanged designation when the designation of the contact state is the in-contact state, and the other of the determinations is not less than the binary classifier by at least the first hysteresis factor or when the designation of the contact state is the out-of-contact state and the other of the determinations is not greater than the binary classifier by at least the second hysteresis factor.

According to a further aspect of the method, passing an electrical current is performed at a power of less than 10 milliwatts.

According to yet another aspect of the method, passing an electrical current is performed at a power of 5-50 watts.

According to a further aspect of the method, the determinations are made at intervals of 200 milliseconds.

There is further provided according to embodiments of the invention ablation apparatus for carrying out the above-described method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Figure 1:
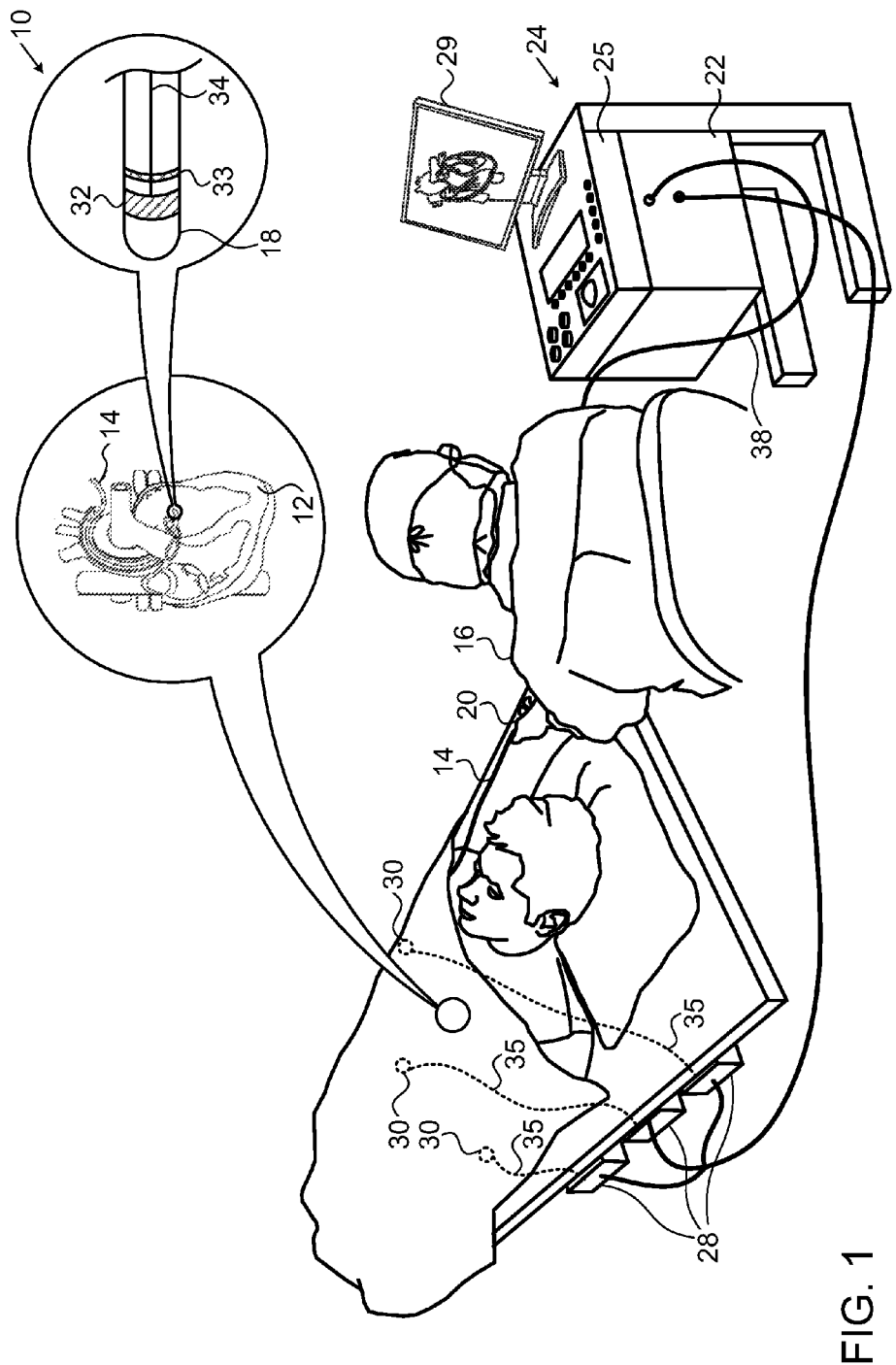
FIG. 1 is a pictorial illustration of a system for performing diagnostic and therapeutic procedures on a heart of a living subject, which is constructed and operative in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24, are disposed between the ablation electrodes 32 and have connections to the cable 34.

Wire connections 35 link the console 24 with body surface electrodes 30 and other components of a positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

As explained in the above-noted U.S. Pat. No. 7,306,593, impedance measurements between the ablation electrode 32 and the endocardial tissue have been found useful in predicting and controlling ablation.

Figure 2:
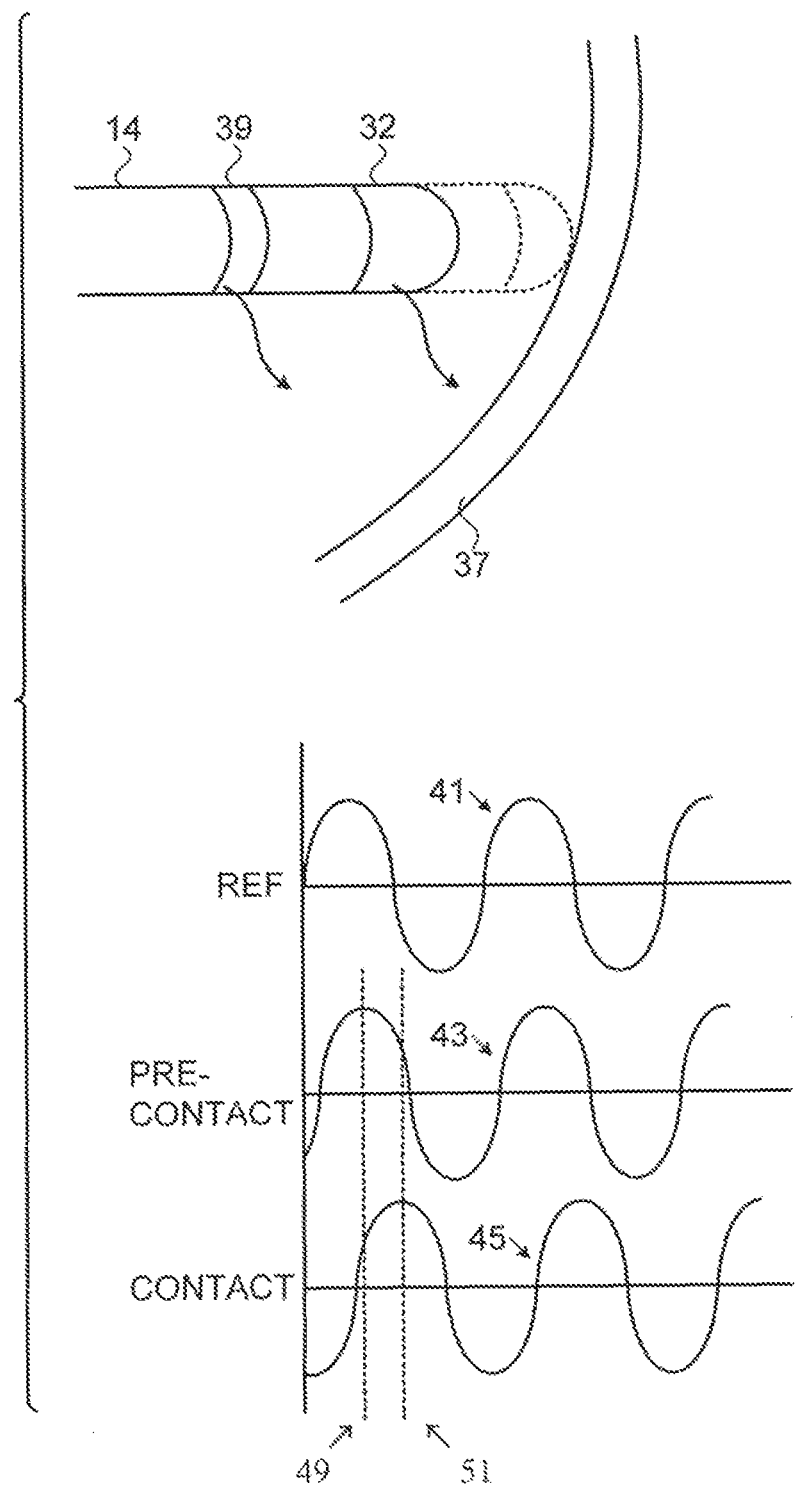
FIG. 2 is a composite drawing illustrating phase relationships of currents passing through an electrode of the catheter as it moves into contact with heart tissue in accordance with an embodiment of the invention.

Reference is now made to FIG. 2, which is a composite drawing illustrating phase relationships of currents passing through the body surface electrodes 30 and an electrode of the catheter 14 as it moves or is moved into contact with wall 37 of heart 12 (FIG. 1) in accordance with an embodiment of the invention. A reference electrode 39 is optionally provided for this purpose. The reference electrode 39 does not contact the wall 37. The electrodes are driven with a signal at a known frequency, which passes through the tissue and is received by the body surface electrodes 30 (FIG. 1) or some other receiving electrode. Waveforms at the right side of FIG. 2 include, from top to bottom, a reference waveform 41 taken from the reference electrode 39, a pre-contact waveform 43 from the ablation electrode 32, taken when the ablation electrode 32 is out of contact with the wall 37, and a contact waveform 45, taken when the ablation electrode 32 is in mechanical contact with the wall 37. Further details regarding the significance of such phase relationships are described in commonly assigned copending application Ser. No. 13/343,024, entitled "Contact Assessment Based on Phase Measurement", which is herein incorporated by reference.

Impedance phase shifts are indicated by displacement of vertical lines 49, 51 drawn through corresponding maxima of the pre-contact waveform 43 and the contact waveform 45. The phase shifts occur when the ablation electrode 32 or the sensing electrode 33 (FIG. 1) is brought into contact with the wall 37. Phase measurement of this sort can be used not only to verify tissue contact, but also to check the progress of ablation. The phase angle of a current passing between the ablation electrode 32 and the tissue can be determined using an nMARQ™ catheter, in combination with a multi-channel RF generator and the above-noted CARTO 3 System. Alternatively, the phase may be determined by any of the phase determination methods described in the above mentioned U.S. Patent Application Publication Nos. 2008/0288038 and 2008/0275465, which are herein incorporated by reference.

Figure 3:
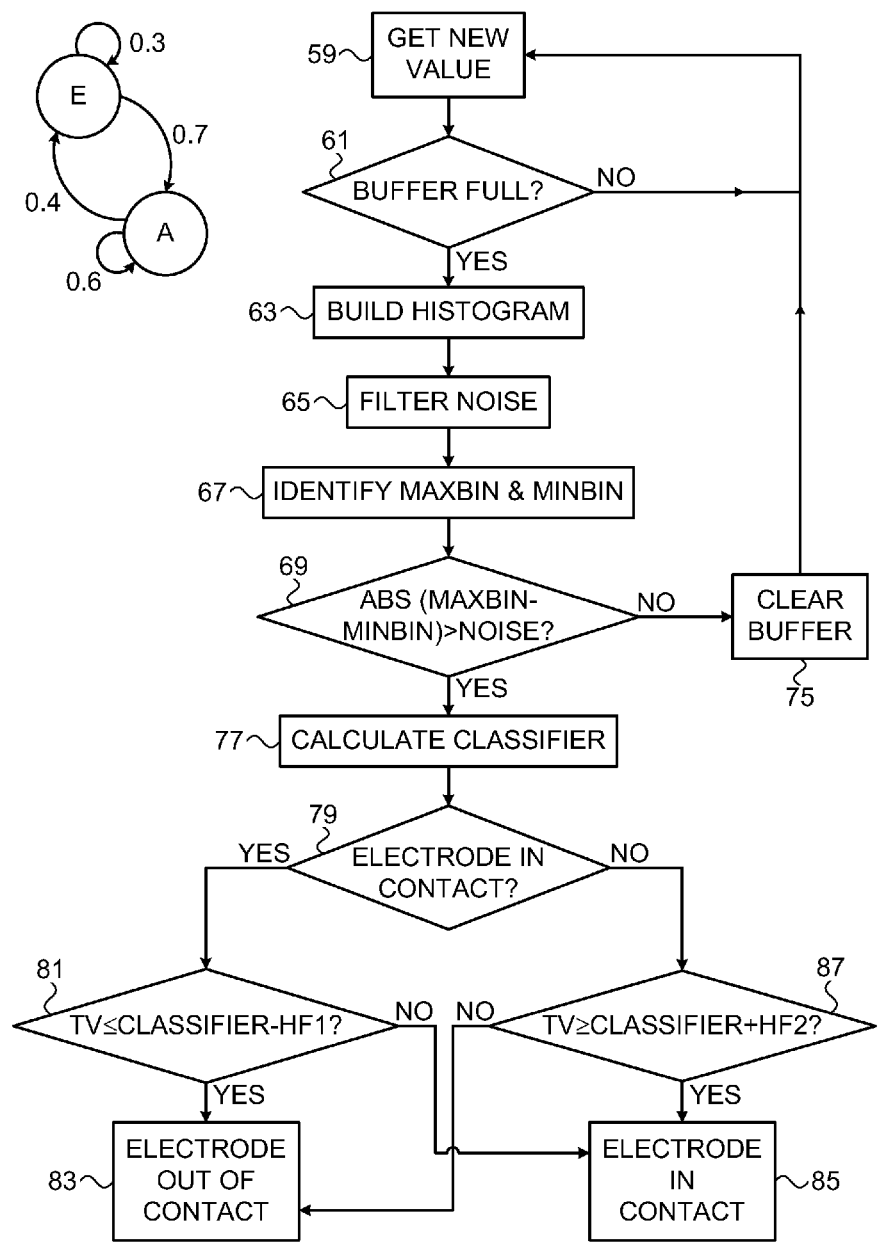
FIG. 3 is a composite diagram including a flow chart of a method of determining contact between a catheter electrode and target tissue in accordance with an embodiment of the invention.

Reference is now made to FIG. 3, which is a composite diagram including a flow chart of a method of determining contact between a catheter electrode and target tissue in accordance with an embodiment of the invention. The diagram illustrates a Markov chain, which is a mathematical system that undergoes transitions among a finite or countable number of possible states. It is a random process characterized as memoryless, in which a subsequent state depends only on the current state, and not on the sequence of events or state changes that preceded it. This specific kind of "memorylessness" is called the Markov property. A Markov chain is a sequence of random variables X1, X2, X3, having the Markov property, namely that, given the present state, the future and past states are independent. Formally:

$$Pr(X_{n+1}=x|X_1=x_1, X_2=x_2, \ldots, X_n=x_n)= Pr(X_{n+1}=x|X_n=x_n)$$

The possible values of $X_i$ form a countable set S called the state space of the chain. In the example of FIG. 3, two states "E" and "A" are shown. The probability of being in a state after an event depends on the current state. If the current state is state E than the probability of remaining in state E is 0.3, whereas if the current state is state A, the probability of transitioning to state E is 0.4.

Determination of a contacting or non-contacting state of a cardiac catheter electrode can be achieved using a Markov state machine having binary states, "1" representing useful contact between an electrode and endocardium, and "0" representing an out-of-contact state, i.e., a state in which there is not useful contact between the electrode and the endocardium. The term "useful contact" is used for convenience to indicate a sufficiently secure contact between the electrode and the endocardium to accomplish an intended objective, e.g., ablation or mapping.

The Markov state machine may be defined as follows, wherein:

P1=Probability of 1 when the last indication was 1.
P2=Probability of 1 when the last indication was 0.
P3=Probability of 0 when the last indication was 1.
P4=Probability of 0 when the last indication was 0.

The estimation of P1, P2, P3, P4 can be accomplished using the process described below. The process steps are shown in a particular linear sequence in FIG. 3 for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the process.

The process involves analysis of multiple impedance phase measurements of an electrical path between the catheter and the body of the subject extending through the target tissue. In general impedance to an alternating current may be represented in polar form by:

$$Z=|Z|e^{j\theta}$$

The process described with reference to FIG. 3 is principally concerned with the argument θ, which gives the phase difference between voltage and current. The object is to determine which of two possible contact states exists between the catheter electrode and the endocardium: an in-contact state and an out-of-contact state. Generally the procedure begins under the assumption that the electrode is out-of-contact, in which case the motion of the heart during the cardiac cycle can be expected to bring the electrode into contact with the endocardium when some of the readings are taken. Alternatively, if it is assumed that the initial contact state of the electrode is in-contact, then the motion of the heart during the cardiac cycle can be expected to place the electrode into an out-of-contact relationship with the endocardium. In any case it is expected that sometimes during the readings the contact state will fluctuate.

Figure 4:
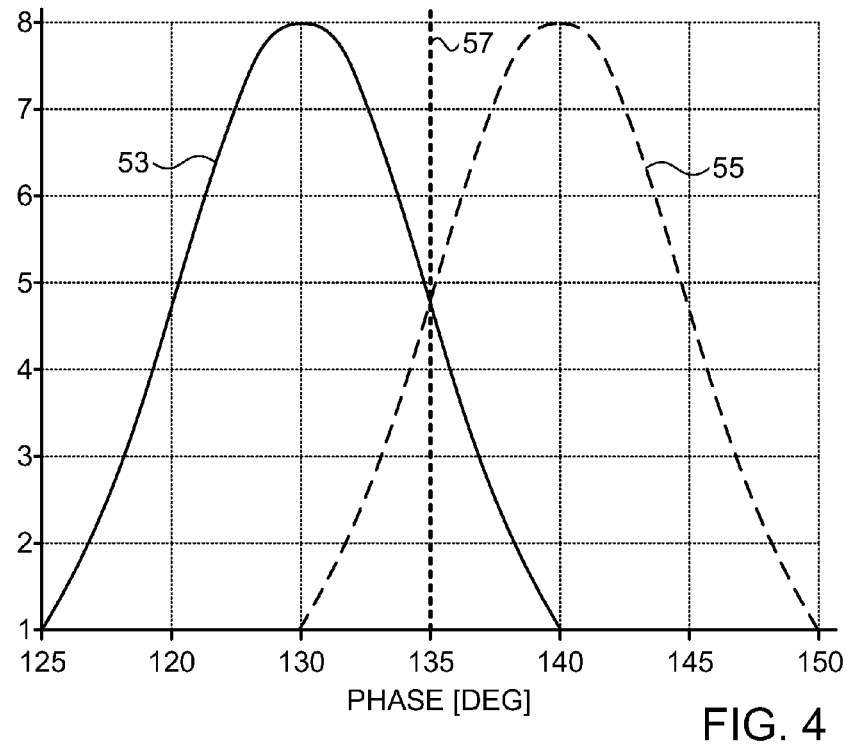
FIG. 4 is a prospective example showing probability distributions of impedance phase measurements taken from a cardiac catheter operating in accordance with an embodiment of the invention.

Reference is now made to FIG. 4, which is a prospective example of probability distributions of impedance phase measurements taken from a cardiac catheter operating in accordance with an embodiment of the invention. Distribution curves 53, 55 correspond to cases when the electrode is in an out-of-contact state and an in-contact state, respectively. An optimum binary classifier for the two states is shown as a broken vertical line 57, corresponding to an impedance phase of 135 degrees.

Reverting to FIG. 3, impedance readings are typically taken at 200 ms intervals. Any of the above-noted methods for impedance determination may be used. At initial step 59 a new impedance reading is obtained, and stored in a cyclic buffer. The power requirement for obtaining phase angle readings is a less than 10 milliwatts if the ablator is idle. If the ablator is active then 5-50 watts is required.

Next, at decision step 61, it is determined if the cyclic buffer is full. Typically, 100 readings are stored. If the determination is negative, then control returns to initial step 59. It is generally unnecessary for the operator to adjust the catheter while the buffer is being filled.

If the determination at decision step 61 is affirmative, then control proceeds to step 63. Essentially, a template for constructing a histogram of the impedance data is prepared, adaptively to the phases that were measured. The buffer is scanned and extreme high and low phase values are identified to define limits of a working range of phase angles. The range is then subdivided into bins for the histogram. Twelve bins are suitable, but other values may be used if different granularity is desired. Then the values in the buffer are then assigned to the bins to build the histogram. If desired the histogram may be displayed graphically.

Next, at step 65 the number of readings in respective bins are evaluated in order to filter noise by eliminating from further consideration those bins having fewer readings than a predetermined noise threshold. Then, at step 67 the remaining bins are scanned to identify the two bins having the maximum number (MaxBin) and minimum number (MinBin) of data points. Alternatively, steps 65, 67 may be combined by simply subtracting the noise threshold when determining the maximum and minimum numbers of data points in the bins.

Next, at decision step 69, it is determined if there is a significant difference between the number of data points in the two bins that were identified in step 67. This may be done using the inequality $$\mathrm{Abs}(\mathrm{MaxBin}-\mathrm{MinBin})>\mathrm{Noise},$$

where Noise is the noise threshold.

Additionally or alternatively, decision step 69 can be performed by measuring the variance of the distribution of the current set of readings. If the variance is low, typically 2.5 degrees or less, then it may be inferred that the contact state did not change during the set of readings, and the information provided by current set is inconclusive.

Figure 5:
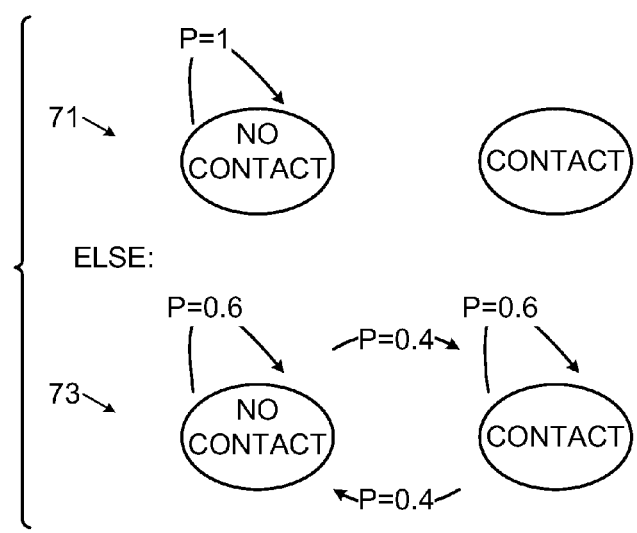
FIG. 5 shows two state diagrams illustrating principles according to an embodiment of the invention.

Reference is now made to FIG. 5, which shows two state diagrams, which are helpful in understanding principles on which an embodiment of the invention is based. An upper diagram 71 illustrates the possibility that the contact state is out-of-contact and unchanging. There is no probability of a transition to an in-contact state. As shown in a lower diagram 73. In a case when the contact state changes as expected, the variance of the impedance readings will be relatively greater, and the corresponding state machine has transitions with exemplary probabilities as shown.

Reverting to FIG. 3, if the determination at decision step 69 is negative, then it is concluded that the current set of readings does not enable a distinction to be made between a non-contact state and a contact state of the electrode. Control proceeds to step 75, where the cyclic buffer is cleared. Control then returns to initial step 59 to obtain another set of readings.

If the determination at decision step 69 is affirmative, then control proceeds to step 77. A binary classifier (T) is established, which is calculated as $$T=(\mathrm{MaxBin}+\mathrm{MinBin})/2.$$

It will be evident that the value of the classifier T is adaptive to the current set of impedance readings. The value of the classifier T is expected to vary among different subjects, and event some extent in different locations within the heart of a particular subject. Therefore, in order to assure that the binary classifier remains accurately defined, the method may be repeated from time to time as the operator moves the catheter to different locations in the heart.

It has been found to be desirable to impose hysteresis on the readings in order to accurately model a transition between an out-of-contact state and an in-contact state (or vice versa). In the following steps the classifier T is compared to the phase angle of a test reading in order to determine if a contact state change has occurred, subject to one or more hysteresis factors. Values of 1.5 degrees for the hysteresis factors are typical. Values of 10% of the dynamic range defined by the extreme values are suitable. However, particularly in the case of catheters were significant amounts of force can be focally applied, the hysteresis factors described below may differ.

The best test reading is the last reading, i.e., the most recent reading taken in the current set of readings. Alternatively, one of the other readings may be chosen as the test reading, for example by random selection or otherwise.

Next, at decision step 79, it is determined if the electrode is in contact with the endocardium. In the first iteration of the method, the contact state may be assumed. Otherwise the contact state is known from a previous iteration of the method.

If the determination at decision step 79 is affirmative, then at decision step 81, the phase of a test reading is compared to the binary classifier. It is determined whether the test reading is less than or equal to the binary classifier adjusted by a first hysteresis factor:

$$TV<=T-\mathrm{HF1},$$

where TV is the test value, T is the classifier that was calculated in step 77, and HF1 is a hysteresis factor. The case where the determination at decision step 79 is negative is described below.

If the determination at decision step 81 is affirmative, then control proceeds to final step 83. A state transition has occurred from an in-contact state to an out-of-contact state. An out-of-contact state is reported.

If the determination at decision step 81 is negative, then control proceeds to final step 85. It is concluded that no contact state transition has occurred. The electrode remains in contact with the endocardium. An in-contact state is reported.

Returning to the discussion of decision step 79, if the determination at decision step 79 is negative, then at decision step 87, it is determined whether the test reading is greater than or equal to the binary classifier adjusted by a second hysteresis factor:

$$TV >= T+HF2,$$

where TV is the test value, T is the classifier that was calculated in step 77, and HF2 is a second hysteresis factor. The hysteresis factor HF2 is typically identical to the hysteresis factor HF1, but this is not necessarily the case.

If the determination at decision step 87 is affirmative, then control proceeds to final step 85. A transition from an out-of-contact state to an in-contact state has occurred. An in-contact state is reported.

If the determination at decision step 87 is negative, then control proceeds to final step 83. The electrode remains out of contact with the endocardium. An out-of-contact state is reported.

It will be appreciated that when the method described above is applied, an indication of the contact state can be achieved without recourse to time-consuming phase calibration procedures. Rather the classification of the states is adaptive to local and subject-specific variations in electrical properties. The procedure is sufficiently reliable to allow ablation to proceed without fear that the ablation current will be delivered while the electrode is out of contact with the endocardium.

Listing 1 presents a computer program in pseudocode for carrying out the method described above.

EXAMPLE 1

Table 1 illustrates a numerical example that illustrates the underlying principal of the process of FIG. 3.

TABLE 1

| Phase Reading | 120 | 120 | 100 | 140 | 120 | 110 | 130 | 120 | 120 |
|---|---|---|---|---|---|---|---|---|---|
| Indication | No Contact | No Contact | No Contact | Contact | Contact | No Contact | Contact | Contact | Contact |

EXAMPLE 2

Figure 6:
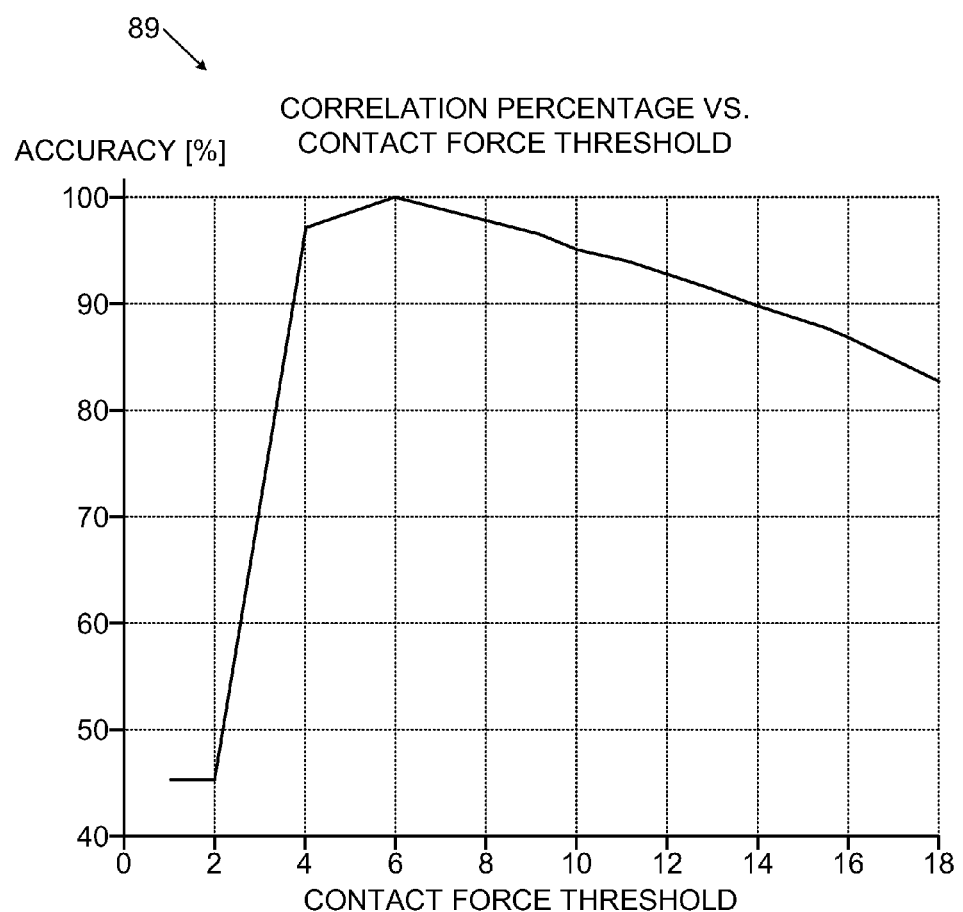
FIG. 6 is a graph illustrating correlation of contact determinations according to an embodiment of the invention with a reference method.

Reference is now made to FIG. 6, which is a graph 89 illustrating correlation of contact determinations using the method described with reference to FIG. 3 with measurements using a conventional contact force catheter with the CARTO 3 System as a reference method. The ThermoCool® SmartTouch™ Contact Force Sensing Catheter, available from Biosense Webster, Inc., is suitable. In FIG. 6, contact force threshold is plotted against accuracy. A contact force threshold of 6 is associated with the highest accuracy of the inventive method.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

---

COMPUTER PROGRAM LISTINGS
Listing 1

```
[n1 n2]=hist(B(end-hist_depth:end, 1), number_of_bins);
// n1- number of points in each bin, n2- range of each bin
For j=1:length(n1)
  if n1(j)>=minimal_points_for_setting_threshold
    min=n2(j);
    break
  end
end
for j=length(n1):-1:1
  if n1(j)>=minimal_points_for_setting_threshold // usually 3
    max=n2(j);
    break
  end
end
threshold=(max+min)/2;
if abs(max-min)>=noise_var // noise_var is experimentally
preset constant
  if (B(end,1)>=threshold+hyst_width)
    contact=1;
  elseif (B(end,1)<threshold-hyst_width)
    // hyst_width- perset constant- usually 2 deg.
    contact=0;
  end
end
```

---

The invention claimed is:

1. A method of cardiac catheterization, comprising the steps of:

inserting a probe into a heart of a living subject, the probe having an electrode;

memorizing a designation of a contact state between the electrode and a wall of the heart as one of an in-contact state and an out-of-contact state;

while the electrode is at the wall, passing an electrical current between the electrode of the probe and another electrode;

making at least three determinations of an impedance phase angle of the electrical current;

identifying a maximum phase angle and a minimum phase angle among the determinations;

defining a binary classifier as a value that is intermediate the minimum phase angle and the maximum phase angle;

when the designation of the contact state is the in-contact state, changing the designation to the out-of-contact state when an other of the determinations is less than the binary classifier by at least a first hysteresis factor;

when the designation of the contact state is the out-of-contact state, changing the designation to the in-contact state when the other of the determinations is greater than the binary classifier by at least a second hysteresis factor; and reporting the changed designation.

2. The method according to claim 1, wherein the other of the determinations is a most recent determination.

3. The method according to claim 1, further comprising the step of determining that a difference between the minimum phase angle and the maximum phase angle exceeds a predefined noise threshold.

4. The method according to claim 1, wherein the value of the binary classifier is midway between the minimum phase angle and the maximum phase angle.

5. The method according to claim 1, wherein the first hysteresis factor is equal to the second hysteresis factor.

6. The method according to claim 1, further comprising the step of reporting an unchanged designation when the designation of the contact state is the in-contact state, and the other of the determinations is not less than the binary classifier by at least the first hysteresis factor or when the designation of the contact state is the out-of-contact state and the other of the determinations is not greater than the binary classifier by at least the second hysteresis factor.

7. The method according to claim 1, wherein passing an electrical current is performed at a power of less than 10 milliwatts.

8. The method according to claim 1, wherein passing an electrical current is performed at a power of 5-50 watts.

9. The method according to claim 1, wherein the determinations are made at intervals of 200 milliseconds.

\* \* \* \* \*